United States Patent [19]

Porcelli et al.

[11] 4,358,411
[45] Nov. 9, 1982

[54] PREPARATION OF CARBONYLATION PRODUCTS

[75] Inventors: Richard V. Porcelli, Yonkers; Vijay S. Bhise, New York, both of N.Y.

[73] Assignee: The Halcon SD Group, Inc., New York, N.Y.

[21] Appl. No.: 53,610

[22] Filed: Jun. 29, 1979

[51] Int. Cl.$^3$ .............................................. C07C 51/12
[52] U.S. Cl. ..................................... 260/546; 260/549
[58] Field of Search ................................ 560/546, 549

[56] References Cited

U.S. PATENT DOCUMENTS 4,115,444  9/1978  Rizkalla ............................... 260/549

Primary Examiner—Robert Gerstl
Attorney, Agent, or Firm—William C. Long; Riggs T. Stewart; Harold N. Wells

[57] ABSTRACT

Carbonylation products such as alkanoic anhydrides, e.g., acetic anhydrides, are produced by carbonylation of esters and/or ethers in the presence of a rhodium or iridium catalyst and an iodine moiety in a reaction zone wherein the reaction mixture is in a continuous boiling state.

3 Claims, No Drawings

PREPARATION OF CARBONYLATION PRODUCTS

This invention relates to carbonylation reactions and is more particularly concerned with the carbonylation of esters and/or ethers to produce alkanoic anhydrides such as acetic anhydride in the presence of rhodium or iridium catalysts and an iodine moiety.

The carbonylation of esters and/or ethers to produce alkanoic anhydrides in the presence of a catalyst comprising a rhodium or iridium component has been relatively recently developed and has been described for example in U.S. Pat. Nos. 3,927,070, 4,046,807 and 4,115,444, as well as in British Pat. No. 1,468,940 and Belgian Pat. No. 839,321. The carbonylation is carried out with carbon monoxide, sometimes also in the presence of hydrogen, and in the presence of an iodine moiety, hydrogen iodide or methyl iodide being generally employed as the iodine moiety in these catalyst systems. The carbonylation is commonly carried out in the liquid phase and the carbonylation product or products are recovered by subjecting the entire liquid carbonylation product mixture, which is removed from the carbonylation zone, to a series of distillations. In the course of this recovery procedure, the rhodium or iridium component and the accompanying relatively non-volatile components of the reaction mixture are obtained as residual products and are recycled to the carbonylation zone. In view of the extremely high cost of catalysts based on rhodium, or irridium, replacement of such catalysts can be effected only at prohibitive cost and it is important, therefore, to minimize any loss or contamination of these valuable materials during the post-carbonylation processing steps. As pointed out in Leach et al. U.S. Pat. No. 4,007,130, when such a process is operated on a continuous basis over extended periods of time, metallic corrosion products tend to build up and to accumulate with the metal-based catalyst stream being recycled from the separation operations to the carbonylation zone. Some of these foreign metals, when present in undesired quantities, tend to interfere with the carbonylation reaction and may have an adverse effect upon the process, e.g. for the reasons discussed in U.S. Pat. No. 4,007,130. That patent proposes to solve the problem by treating the recycled catalyst stream with its accumulated metallic impurities by passing the contaminated catalyst stream through a bed of a cation exchange resin in its hydrogen form. This process is apparently effective for its indicated purpose but it involves the added treating step plus the step of regenerating the cation exchange resin, and the data in the patent make it clear that such treatment can cause the loss of significant quantities of the rhodium or iridium catalyst. Losses may also occur in handling the catalyst in the post-carbonylation treatment of the reaction effluent to recover catalyst for recycling.

While anhydrous systems such as those involved in the preparation of acetic anhydride are less corrosive than the aqueous systems such as described in U.S. Pat. No. 4,007,130, which are significantly corrosive even to nickel alloys and like corrosion-resistant materials of construction, non-aqueous systems tend nevertheless to be corrosive to many metallic surfaces, probably because of the carbon monoxide partial pressure involved, even in product and catalyst separation zones.

Thus, even when using separation zones having surfaces of stainless steel and like normally corrosion-resistant materials, products of corrosion tend rapidly to build-up, unless a significant purge is provided. Fabricating the separation zones and all auxiliary equipment of expensive corrosion-resistant alloys will help to alleviate the problem but this is not an economically-attractive alternative.

It is accordingly an object of the present invention to provide an improved carbonylation process wherein the problems heretofore encountered in liquid phase carbonylation in the presence of rhodium or iridium catalysts are minimized, recovery of the carbonylation products is facilitated and operational difficulties of handling such a valuable catalyst are eliminated.

In accordance with the invention, this and other objects are realized by carrying out the carbonylation reaction with the rhodium or iridium catalyst and an iodine moiety in a boiling reaction zone. A boiling reaction zone is one which is operated under temperature and pressure conditions such that the liquid present is continuously boiling, e.g. is being continuously vaporized, away from the catalyst, and the reaction product effluent is removed from the reaction zone in the vapor state as distinguished from conventional liquid-phase reactions wherein the product effluent is withdrawn as a liquid stream. The boiling reaction zone is also distinguished from a vapor-phase zone wherein the reactants and the reaction products are essentially all in the vapor phase at all times. It has been surprisingly discovered that when the carbonylation is carried out continuously in a boiling reaction zone of the character described, particularly when a catalyst comprising rhodium is employed, the problem of contamination of foreign metals is minimized, there is no loss of catalyst as a result of handling of a catalyst stream or as a result of external treatment of a catalyst stream and, in addition, desired high selectivities to desired carbonylation products are achieved. The use of a boiling reaction zone by eliminating catalyst handling avoids the danger of spills, pump leaks, and the like, which can have serious implications with so costly a catalyst, but are all too often considered necessary occurrences in a typical chemical plant. Furthermore, possible overheating and precipitation of a concentrated catalyst "heel" in the separation bottoms is avoided, since the catalyst is never separately recovered and, therefore, is always at appropriate reaction concentrations in the carbonylation zone.

Carbonylation involving an ester, such as methyl acetate, and carbon monoxide together with an iodine moiety is carried out to produce acetic anhydride under a carbon monoxide partial pressure of 0.1 to 15,000 psi, and in the presence of a rhodium or an iridium catalyst, preferably a rhodium catalyst such as disclosed in Belgian Pat. Nos. 819,455 and 839,321 and in U.S. Pat. No. 4,115,444. For ease of description, the invention will be described in terms of the carbonylation of methyl acetate. It will, of course, be understood that methyl acetate can be replaced or supplemented with dimethyl ether in the feed. It has been observed that the dimethyl ether is converted to methyl acetate in the carbonylation reaction so that it may be considered a methyl acetate precursor. When, therefore, reference is made to methyl acetate as a feed to the carbonylation, it will be understood that the dimethyl ether precursor is also contemplated. The invention is also fully applicable to the carbonylation of other alkyl esters of alkanoic acids such as those described in U.S. Pat. No. 4,115,444, British Pat. No. 1,468,940 and Belgian Pat. No. 819,455.

The rhodium or iridium carbonylation catalyst can be supplied and used in any convenient form, viz. in the zero valent state or in any higher valent form. For example, the catalyst may be the metal itself in a finely-divid form, or as a metal carbonate, oxide, hydroxide, bromide, iodide, chloride, lower alkoxide (methoxide), phenoxide or metal carboxylate wherein the carboxylate ion is derived from an alkanoic acid of 1 to 20 carbon atoms. Complexes of the metals can be employed, e.g. the metal carbonyls, such as iridium and rhodium carbonyls, e.g. hexarhodium hexadecacarbonyl, or as other complexes such as the carbonyl halides, e.g. iridium tri-carbonyl chloride $[Ir(CO)_3Cl]_2$ or chlorodicarbonyl rhodium dimer, or the acetylacetonates, e.g. rhodium acetylacetonate $Rh(C_5H_7O_2)_3$. It will be understood that the foregoing compounds and complexes and classes of compounds and complexes are merely illustrative of suitable forms of the rhodium or iridium catalyst and are not intended to be limiting.

The metal employed may contain impurities normally associated with the commercially available metal or metal compounds, and need not be purified any further. Thus, the commercially available metal or metal compound is suitably employed.

The amount of rhodium or iridium catalyst is in no way critical and is not a parameter of the process of the invention and can vary over a wide range. As is well known to persons skilled in the art, the amount of catalyst used is that which will provide the desired suitable and reasonable reaction rate since reaction rate is influenced by the amount of catalyst. However, essentially any amount of catalyst will facilitate the basic reaction and can be considered a catalytically-effective quantity. Typically, however, the catalyst is employed in the amount of 1 mol per 10 to 10,000 mols of ester, preferably 1 mol per 50 to 10,000 mols of ester, and most preferably 1 mol per 50 to 2,000 mols of ester.

The carbon monoxide is preferably employed in substantially pure form, as available commercially, but inert diluents such as carbon dioxide, nitrogen, methane, and noble gases can be present if desired. The presence of inert diluents does not affect the carbonylation reaction but their presence makes it necessary to increase the total pressure in order to maintain the desired CO partial pressure. The carbon monoxide, like the other reactants, should, however, be essentially dry, i.e. the CO and the other reactants should be reasonably free from water. The presence of minor amounts of water such as may be found in the commercial forms of the reactants is, however, acceptable. Hydrogen, which may be present in small amounts as an impurity, is not objectionable and even may tend to stabilize the catalyst. Indeed, it is desirable to have minor amounts of hydrogen present in the carbonylation zone during the carbonylation reaction. It has been found that hydrogen, as mentioned, stabilizes the catalyst and maintains its activity at a high level. Hydrogen partial pressures up to about 200 psi can be employed for this purpose but ordinarily hydrogen partial pressures above about 50 to 60 psi are not necessary for this purpose.

It has been previously found that the activity of the rhodium or iridium catalysts described above can be significantly improved, particularly with respect to reaction rate and product concentration, by the concurrent use of a promoter. Effective promoters include the elements having atomic weights greater than five of Groups IA, IIA, IIIA, IVB, VIB, the non-noble metals of Group VIII and the metals of the lanthanide and actinide groups of the Periodic Table. Particularly preferred are the lower atomic weight metals of each of these groups, e.g. those having atomic weights lower than 100, and especially preferred are metals of Groups IA, IIA and IIIA as are metals of Group VIB and the non-noble metals of Group VIII. In general, the most suitable elements are lithium, magnesium, calcium, titanium, chromium, iron, nickel and aluminum. The particularly preferred elements are lithium and chromium. The promoters may be used in their elemental form, e.g. as finely-divided powdered metals, or they may be employed as compounds of various types, both organic and inorganic, which are effective to introduce the element into the reaction system. Thus, typical compounds of the promoter elements include oxides, hydroxides, halides, e.g. bromides and iodides, oxyhalides, hydrides, alkoxides, and the like. Especially preferred organic compounds are the salts or organic monocarboxylic acids, e.g. alkanoates such as acetates, butyrates, decanoates and laurates, benzoates, and the like. Other compounds include the metal alkyls, carbonyl compounds as well as chelates, association compounds and enol salts. Particularly preferred are the elemental forms, compounds which are bromides or iodides, and organic salts, e.g. salts of the mono-carboxylic acid corresponding to the anhydride being produced. Mixtures of promoters can be used, if desired, especially mixtures of elements from different Groups of the Periodic Table. The exact mechanism of the effect of the promoter, or the exact form in which the promoter acts, is not known but it has been noted that when the promoter is added in elemental form, e.g. as a finely-divided metal, a slight induction period is observed.

The quantity of promoter can vary widely but preferably it is used in the amount of 0.0001 mol to 10 mols per mol of rhodium or iridium catalyst, most preferably 0.001 to 10 mols per mol of catalyst.

In accordance with the process of the invention, the rhodium or iridium catalyst and any metallic promoter present, such as chromium, remains at all times in the carbonylation zone and does not have to be handled or recovered exteriorly of the carbonylation zone for recycle as pointed out above, a very important feature from the standpoint of minimizing loss of catalyst and eliminating catalyst handling problems which inevitably occur at least to some extent in carbonylation processes wherein the catalyst is recovered from the reactor effluent and recycled.

The activity of the rhodium or iridium catalysts described above is also significantly improved, particularly with respect to reaction rate and product concentration, catalyst stability and corrosion inhibition, by the use of an organic promoter, and particularly advantageous is the concurrent use of a promoter combination or co-promoter system containing a metal component which is a metal of Groups IVB, VB and VIB, and the non-noble metals of Group VIII, in any of the forms described above, in association or combination with an organo-nitrogen compound or an organo-phosphorus compound wherein the nitrogen and the phosphorus are trivalent.

The organic promoter can, in its broader sense, be any organo-nitrogen or organo-phosphorus compound wherein the nitrogen and phosphorus are trivalent. Preferably, however, the organo-nitrogen promoter is an amine, especially a tertiary amine of the formula

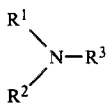

wherein $R^1$, $R^2$ and $R^3$ are the same or different and are alkyl, cycloalkyl, aryl or acyl groups which may be substituted by non-interfering groups, preferably having up to 20 carbon atoms, such as trimethylamine, triethylamine, triphenylamine, ethylenediamine tetraacetic acid, and the like, or a heterocyclic amine such as pyridine, picoline, quinoline, methylquinoline, hydroxy quinoline, pyrrole, pyrrolidine, pyrrolidone, and the like, or an imidazole, such as imidazole, methyl imidazole and the like, or an imide of a carboxylic acid which may be monobasic or polybasic and which may be aliphatic or aromatic and preferably contains up to 20 carbon atoms, such as acetic acid, succinic acid, phthalic acid, pyromellitic acid, e.g., N, N-dimethylacetamide, succinimide phthalimide and pyromellitic diimide, or a nitrile or amide which may be aliphatic or aromatic and preferably contain up to 20 carbon atoms, e.g., acetonitrile, hexamethyl phosphoric triamide, and like imides, nitriles, and amides, or an oxime such as cyclohexanone oxime, and the like. It will be understood, however, that higher molecular weight promoters, e.g. polymeric forms of the organo-nitrogen compounds, may be used such as polyvinylpyridine, polyvinyl pyrrolidone, and the like.

The organo-phosphorus promoter is preferably a phosphine of the formula

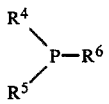

wherein $R^4$, $R^5$ and $R^6$ may be the same or different and are alkyl, cycloalkyl, aryl groups, amide groups or halogen atoms, preferably containing 1 to 20 carbon atoms in the case of alkyl and cycloalkyl groups and 6 to 18 carbon atoms in the case of aryl groups. Typical phosphines include trimethylphosphine, tripropylphosphine, tributyl phosphine, tricyclohexyphosphine and triphenylphosphine.

Although, preferably the organic promoters are added separately to the catalyst system, it is possible to add them as complexes with the Group VIII noble metal such as the trichloro trispyridine rhodium, tris(triphenyl phosphine) rhodium, chlorotris(triphenyl phosphine) rhodium, and chlorocarbonyl bis(triphenyl phosphine) rhodium, and like complexes. Both free organic promoters and complexed promoters can also be used. Indeed, when a complex of the organic promoter and the rhodium or iridium catalyst is used, it is desirable to add free organic promoter as well. The amount of organic promoter will generally lie in the ranges referred to above for the metal promoter except that preferably up to 50 mols per mol of catalyst are employed.

The ratio of ester to the halide in the reaction system can vary over a wide range. Typically, there are used 1 to 500 mols, preferably 1 to 200 mols of ester per mol of halide reactant. By maintaining the partial pressure of carbon monoxide at the values specified, adequate amounts of the reactant are always present to react with the hydrocarbyl halide.

The carbonylation step is readily carried out in a single reaction zone to which an iodine source, e.g. methyl iodide, and the methyl acetate are both charged and are heated together in the presence of carbon monoxide and in the presence of the rhodium or iridium catalyst. It will be understood that the hydrocarbyl iodide may be formed in situ and the iodide may thus be supplied to the system not only as the hydrocarbyl iodide but the iodine moiety may also be supplied as another organic iodide or as the hydro-iodide or other inorganic iodide, e.g. salts, such as the alkali metal or other metal salts, or even as elemental iodide.

The temperature of the reaction mixture is selected to keep the reaction mixture under continuously boiling conditions, i.e. to maintain continuous vaporization of the liquid reaction mixture, at the total pressure and total gas flow rate employed. Ordinarily, the temperature will lie within the range of 100° and 200° C. Higher temperatures can be employed but there is no particular advantage in their use. The time of reaction is not a parameter of the process and depends largely upon the temperature employed, but typical residence times, by way of example, will generally fall in the range of 0.1 to 20 hours.

The feed of gases to the carbonylation zone, e.g. carbon monoxide, hydrogen if used, and recycle gases, is suitably effected by directing the gases into the liquid reaction medium so that the gases pass upwardly through it. This not only provides agitation but facilitates control of the partial pressures of the gases. The reaction is carried out under superatmospheric pressure but excessively high pressures, which require special high-pressure equipment, are not necessary. In general, the reaction is effectively carried out by employing a carbon monoxide partial pressure which is preferably 5 to 2,000 psi, although carbon monoxide partial pressures of 0.1 to 15,000 psi can also be employed. The total pressure is that required to provide the desired CO partial pressure and that required to maintain the liquid phase but to allow boiling conditions. Typically, total pressures up to about 3,000 psig are used but most preferably they are at most about 1,000 psig. The reaction can be advantageously carried out in an autoclave or similar apparatus.

It will be apparent that the carbonylations referred to above are carried out under substantially anhydrous conditions. The presence of minor amounts of water, however, such as may be found in commercially available reactants, is permissible. Normally, however, the presence of more than 5 mol % of water in any one or more of the reactants should be avoided, the presence of less than 3 mol % of water desired, and the presence of less than 1 mol % is preferred.

The effluent from the carbonylation zone is entirely gaseous, i.e. it is composed of the non-condensible gases in the reaction system such as carbon monoxide and hydrogen if present, as well as vaporized organic compounds including the product acetic anhydride, unreacted methyl acetate, methyl iodide, and organic promoter if present. Ordinarily, the promoter forms a complex with the rhodium or iridium catalyst which is non-volatized and thus remains in the carbonylation zone. The effluent is cooled to cause the condensation of the condensible components and to leave substantially only the non-condensible gases which are recycled to the carbonylation zone along with fresh supplies of carbon monoxide, and hydrogen if used, to maintain the prescribed partial pressures during carbonylation. A purge of the recycled gases may be taken in conventional manner to prevent the build-up of contaminating gases which may have been present in the carbon monoxide or hydrogen feed to the system such as nitrogen or may have been produced in the carbonylation reaction itself such as methane. The condensed portion of the effluent is then subjected to conventional fractional distillation to separate it into its individual components or fractions and the unreacted methyl acetate and the methyl iodide are recycled for reuse.

What is significant in the carrying out of the process of the invention is that there is no separation or handling of catalyst exteriorly of the carbonylation zone so that the catalyst would not become contaminated with corrosion products resulting from contact with exterior surfaces and there are no problems caused by the necessity for recycling catalyst after it has been separated from the reaction effluent. There is thus provided a process which will yield acetic anhydride with high selectivity while avoiding the previously discussed problems relating to corrosion products and catalyst handling.

The following examples of specific application will serve to provide a fuller understanding of the invention but it will be understood that these examples are given for illustrative purposes only, however, and are not to be interpreted as limitative of the invention. In the examples, all parts are by weight unless otherwise indicated.

EXAMPLE I

This example illustrates the advantage of utilizing a boiling reaction zone in order to eliminate the contamination of catalyst by corrosion. Using a reactor in the form of a 1-liter stirred autoclave (constructed of Hastelloy C), provided with an inlet for liquid, a line connected to a source of carbon monoxide and hydrogen, and recycle gas, methyl acetate is carbonylated in the presence of a catalyst composed of rhodium trichloride trihydrate, tributyl phosphine and chromium hexacarbonyl, as follows. The reactor is charged with approximately 670 ml of approximately 20 parts methyl iodide and 80 parts methyl acetate containing approximately 0.007 mol (expressed as Rh) of rhodium trichloride trihydrate, 0.118 mol of tributyl phosphine and 0.007 mol (expressed as Cr) of chromium hexacarbonyl, and then heated for one hour at 160° C. Continuous operation is then begun with a feed of about 180 g./hr. methyl iodide and about 800 g./hr. methyl acetate. Carbon monoxide is supplied to the reactor to maintain partial pressure of 420 psi and similarly hydrogen is supplied continuously to maintain a hydrogen partial pressure of 55 psi. The reaction product effluent is removed continuously from the reaction zone in the vapor state, condensed and collected at the rate of about 1,000 g./hr. of condensate. The non-condensed portion of the effluent is recycled and combined with make-up carbon monoxide and hydrogen to provide the above-indicated partial pressures. A small purge of the recycle gas is taken to prevent build-up of gases other than carbon monoxide and hydrogen. Under these conditions, it is found that methyl acetate is converted to acetic anhydride with a selectivity of about 95%. After 1,500 hours of operation, the reaction mixture is analyzed for corrosion products and none are found nor does the autoclave show any signs of corrosive attack.

COMPARATIVE EXAMPLE A

This example illustrates the contamination caused to rhodium catalyst when the entire liquid carbonylation product mixture is treated to a distillation step to recover and recycle catalyst back to the reactor. Using a reactor in the form of a 1-gallon stirred autoclave (constructed of Hastelloy C) provided with an inlet for liquid feed, and a line connected to a source of carbon monoxide and hydrogen, methyl acetate is carbonylated in the presence of a catalyst composed of rhodium trichloride trihydrate, tributyl phosphine and chromium hexacarbonyl, as follows. The reactor is charged with approximately 1.8 liters of a mixture of 20 parts of methyl iodide and 80 parts of methyl acetate containing approximately 0.03 mol (expressed as Rh) or rhodium trichloride, trihydrate, 1.44 mol of tributyl phosphine and 0.03 mol (expressed as Cr) of chromium hexacarbonyl, and heated for 1 hour at 160° C. under a partial pressure of carbon monoxide of approximately 420 psi and a hydrogen partial pressure of approximately 55 psi. Continuous operation is then begun with a feed of 225 g./hr. methyl iodide and 910 g./hr. methyl acetate. Carbon monoxide alone is supplied to the reactor at this time to maintain a continuous carbon monoxide partial pressure of about 440 psi (total pressure 550 psig). The liquid reaction mixture is continuously withdrawn from the reactor at the rate of 13,300 g./hr. and passes to a flash distillation chamber maintained under a pressure of 75 psig and a temperature of 130° C. A partial pressure of 15 psi hydrogen and 21 psi of carbon monoxide is maintained in the flash distillation chamber which is constructed of 317L stainless steel in order to maintain catalyst activity. Approximately 1,180 g./hr. of the liquid fed to the flash chamber is volatilized, condensed and collected and about 11,150 g./hr. of non-volatilized liquid containing catalyst is recycled to the reactor. Under these conditions, it is found that methyl acetate is converted to acetic anhydride with a selectivity of about 96%. After 1,000 hours of operation, it is found that the reactor shows no signs of corrosion but analysis of the recycle liquid stream shows corrosion products from the flash distillation chamber building up at a rate of about 1 ppm per hour.

The preceding comparative example involves operation in the "once-through" mode with respect to the non-condensible gases which are separated from the condensible components of the vapors from the flash distillation step, i.e. the non-condensible gases are not recycled as they are in Example I. This, of course, has an obvious economic drawback since the amount of non-condensible gas discarded in this fashion is large (roughly of the same order of magnitude as the condensible components on a molar basis) and represents an economic penalty. When, however, these non-condensible gases, after separation from the condensible components and purging as in Example I, are recycled to the carbonylation zone and to the flash distillation zone to replace a portion of the fresh gas "make-up," the selectivity to acetic anhydride is found to decrease significantly to a value of about 75%, again representing an economic penalty.

What is claimed is:

1. In the carbonylation of methyl acetate or dimethyl ether in a carbonylation zone in the presence of a rhodium or iridium catalyst to produce acetic anhydride, the improvement which comprises carrying out the reaction in the liquid phase under temperature and pressure conditions such that boiling conditions are maintained and the entire reaction zone effluent from the carbonylation zone is in vapor form but the catalyst remains in the carbonylation zone, cooling the vaporous effluent to condense condensible components therefrom, recycling at least some of the non-condensible components, and separating the condensible components to recover product acetic anhydride therefrom.

2. A process as defined in claim 1, wherein the reaction is carried out at a temperature of at least 100° C. and under a partial pressure of carbon monoxide of at least 5 psi.

3. A process as defined in claim 2, wherein the partial pressure of carbon monoxide is in the range of 5 to 1,000 psi.

* * * * *

UNITED STATES PATENT AND TRADEMARK OFFICE
CERTIFICATE OF CORRECTION

PATENT NO. : 4,358,411

DATED : November 9, 1982

INVENTOR(S) : Richard V. Porcelli et al

It is certified that error appears in the above-identified patent and that said Letters Patent is hereby corrected as shown below:

Col. 3, line 35 - "10,000" should be --100,000--

Signed and Sealed this

Eighteenth Day of October 1983

[SEAL]

Attest:

GERALD J. MOSSINGHOFF

Attesting Officer     Commissioner of Patents and Trademarks